United States Patent [19]

Weiss

[11] Patent Number: 4,643,188

[45] Date of Patent: Feb. 17, 1987

[54] SURGICAL DEVICE FOR PERFORMING EMERGENCY CRICOTHYROTOMIES AND TRACHEOTOMIES

[76] Inventor: Sol Weiss, 17227 Quesan Pl., Encino, Calif. 91316

[21] Appl. No.: 701,914

[22] Filed: Feb. 14, 1985

[51] Int. Cl.[4] .................... A61B 17/32; A61B 17/34
[52] U.S. Cl. ............................ 128/305.3; 128/329 R
[58] Field of Search .......... 128/305.3, 200.26, 329 R; 604/158, 164

[56] References Cited

U.S. PATENT DOCUMENTS

| 300,285 | 6/1884 | Russell | 128/305.3 |
| 2,840,082 | 6/1958 | Salvatore | 128/305.3 X |
| 3,688,773 | 9/1972 | Weiss | 128/305.3 |

Primary Examiner—Michael H. Thaler
Attorney, Agent, or Firm—Gerald L. Price

[57] ABSTRACT

An improved surgical device for performing emergency cricothyrotomies and tracheotomies. The device includes a holder for a stylet or tube which holder includes a two-part needle attached to a pair of handles, each handle including one part of the needle, which handles can be spread apart for insertion of a tube or stylet between the needle parts. The tube or stylet is then held between the needle parts. When it is desired to remove the device from the patient, one of the handles having its needle part can be removed from the other handle having its needle part without disturbing the tube or stylet held between the needle parts. In this manner, sutures can be easily made around a chest or throat opening in which the device has been inserted since only the tube remains in place.

1 Claim, 33 Drawing Figures

SURGICAL DEVICE FOR PERFORMING EMERGENCY CRICOTHYROTOMIES AND TRACHEOTOMIES

BACKGROUND OF THE INVENTION

1. Field of the Invention

The invention relates to surgical devices; and, more particularly, to a device for performing emergency cricothyrotomies and tracheotomies.

2. Description of the Prior Art

Tracheostomy is an operation for the purpose of relieving an obstruction of the respiratory passage. One such prior art device is described in detail in U.S. Pat. No. 3,688,773 of which I am the inventor. In U.S. Pat. No. 3,817,250, of which I am co-inventor, an improvement of the device of my earlier patent is described. In general, both these prior art devices comprise an expandable needle, enlarged in a rear section and tapering to a sharp point for puncturing the skin and tissue of a patient. The sharp end of the needle is used to make the puncture and the entire needle is inserted into the trachea. An air tube is then inserted into the needle, expanding the same, and into the tracheal area to allow the patient to breathe.

In my copending application Ser. No. 701,916 filed Feb. 14, 1985 I described an improved apparatus and method for performing an emergency cricothyrotomy comprising a tracheostomy device which can be inserted into a patient's neck without danger of puncture of the posterior wall and which permits insertion of an airway tube without popping out of the device from the incision in the patient's neck or penetrating the posterior wall. An airway tube can be quickly and easily substituted for another airway tube of differing internal diameter without the need for redefining the puncture area or utilization of additional instrumentation. If desired, a closed system can be quickly and easily coupled to the device without the need for making a bigger opening in the patient's neck.

It is well known that young children have airways problems different from adults since their anatomy is not the same. These differences in anatomy create special problems when performing crictothyrotomies/tracheotomies on young children. Children have proportionally larger heads and tongues; they have epiglottis that protrude backward at an angle of forty-five degrees; larynxes that are more cephalad; cricoid cartilages that are narrower than the glottis; and vocal cords that are more susceptible to ulceration and trauma.

A newborn's glottis measures about 7 mm anterior-posterior and 4 mm transversely. This means that a mere 1 mm of mucosal edema reduces the glottal airway to 35 percent of its normal opening. The subglottic larynx of the infant is only 5 mm in diameter.

The cephalad position of the infant's larynx makes him or her an obligate nose-breather and creates wider angulation between the tongue and the larynx. The infant's cricothyroid is not easily palpable and is too small to be useful as an emergency airway.

The arytenoids are larger than an adult's in relation to the larynx. The epiglottis and other supraglottic structures have loosely attached mucous membranes with softer tissues and looser tissue planes, which facilitate more rapid development of edema and obstruction than do an adult's. The subglottic conus elasticus laryngis is also more prone than an adult's to develop edema. The entire larynx, including its cartilaginous skeleton, is softer and readily collapsible. The proximity of mediastinal structures to the larynx increases the risk of complications of tracheotomy, such as pneumothorax, mediastinal emphysema, and vascular erosion.

The infant has less respiratory reserve than the older child and the adult. The infant's resting oxygen consumption per unit of weight is twice that of the adult. Infants and young children have high peripheral airway resistance and greater tendency to airway obstruction because the diameter of the distal airway remains relatively small from birth to about 5 years of age. Finally, the infant has about twice the surface area per unit of weight as the adult, thus twice the heat loss.

Thus, it can be seen that many surgical instruments require a large space to operate in but a young child's anatomy only allows for a very small area in which to perform cricothyrotomies/tracheotomies. In such operations, it is necessary for the angle of penetration to be as close to 90 degrees to the anterior neck as possible. There is a need for an improved surgical instrument for performing such operations in young children. Resuscitative efforts in young children require the institutuion of quick, safe and adequate airways which can provide adequate suctioning. An instrument that is simple to insert, that protects against overpenetration, minimizes bleeding, causes minimal tissue damage and offers airways of different sizes is necessary. Surgical cricothyrotomy/tracheotomy is a dangerous and difficult method of airway management in a young child. Nasal and oral intubation for managing a blocked airway are not always successful. If one is unable to open the airway and ventilate the small child within 4 to 6 minutes, the results may be lethal. Causes for the surgical intervention may be due to inability to intubate in the presence of complete airway obstruction for any reason, such as foreign bodies that cannot be removed, trauma(-penetrating, burns or blunt), swelling, epiglottitis and extubation difficulties.

Puncture of the cricothyroid membrane has been acknowledged as a preferred method of establishing an emergency airway in young children. The cricothyroid membrane, however, cannot always be found in young children under the ages of 12 to 14 and, therefore, penetration may be necessary at the inferior portion of the cricothyroid or into the first tracheal ring.

The trachea of the small child is softer and more readily collapsible. The proximity of the mediastinal structures to the area of tracheotomy increases the risk such as pneumothroax, mediastinal emphyseme and vascular complications. The trachea is more movable an tends to remain small in its diameter until 5 years of age. The cricothyroid membrane is near the C4 level in small children and moves to the C6 level by adulthood.

An ideal instrument for accomplishing an emergency cricothyrotomy/tracheotomy in the young child, ages 1 to 8, would have to be adaptable to perform the procedure in a small area. It would also have to be adaptable to patients of varying sizes, minimize tissue damage and bleeding, reduce the danger of overpenetration and assure simplicity of use. Such a device should establish airflow instantaneously and remain sterilized yet ready for immediate use.

In addition to the foregoing problems performing such operations, there is a need for improved surgical instruments for performing thoracostomies. In this operation, negative air pressure in the chest cavities creates special problems. In such operations, it is difficult to remove the trocar and chest tube. The flesh or walls of the puncture grasps the chest tube and makes it difficult to remove the holder for the tube so that the wound surrounding the tube can be sutured. There is thus a need for an improved surgical device for performing thoracostomies where the holder for the tube can be easily removed without the need for removing or disturbing the tube.

Thus, there is a need for an improved surgical instrument that is useful in both cricothyrotomies and thoracostomies where the holder for the respective tubes can be removed easily and quickly without the need for disturbing or removing the tube.

SUMMARY OF THE INVENTION

It is an object of this invention to provide an improved surgical evice particularly suited to performing cricothyrotomies/tracheotomies on young children.

It is a further object of this invention to provide an improved surgical device particularly suited to performing thoracostomies and laparoscopies, especially where the escape of gas or air must be controlled.

It is still further an object of this invention to provide a surgical device which avoids overpenetration in carrying out tracheotomies/cricothyrotomies on young children.

It is still another object of this invention to provide a surgical device for performing tracheotomies/cricothyrotomies and thoracostomies and laparoscopies where the depth of penetration is controlled at all times.

It is still further an object of this invention to provide a surgical device for performing tracheotomies/cricothyrotomies and thoracostomies and laparoscopies wherein, once the airway tube is in place, the holder therefor can be quickly and easily removed without disturbing the tube.

These and other objects are preferably accomplished by providing a surgical device having a holder for a stylet or tube which holders includes a two-part needle attached to a pair of handles, each handle including one part of the needle, which handles can be spread apart for insertion of a tube or stylet between the needle parts. The tube or stylet is then held between the needle parts. When it is desired to remove the device from the patient, one of the handles having its needle part can be removed from the other handle having its needle part without disturbing the tube or stylet held between the needle parts. In this manner, sutures can be easily made around a chest or throat opening in which the device has been inserted since only the tube remains in place.

DESCRIPTION OF THE PREFERRED EMBODIMENT

Figures 1, 2, 33:
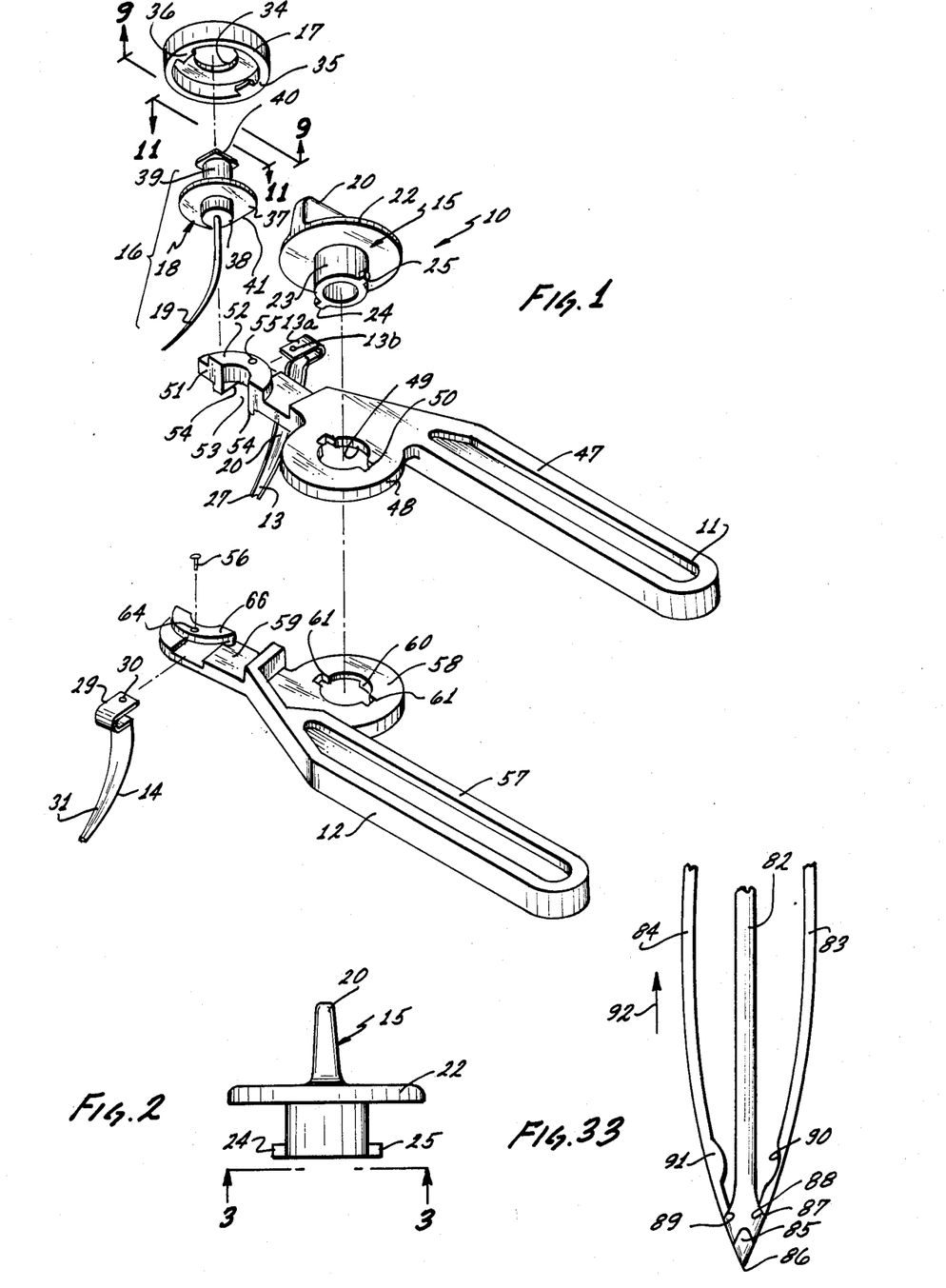
FIG. 1 is an exploded view of an improved surgical device in accordance with the teachings of the invention.
FIG. 2 is a vertical view of the key alone of FIG. 1.
FIG. 33 is a vertical view of a further modified stylet and needle therefore.

Referring now to FIG. 1 of the drawing, an improved surgical device or instrument 10 is shown in exploded view. Device 10 includes a pair of handle portions 11,12, handle portion 11 being referred to as the upper handle portion and handle portion 12 being referred to as the lower handle portion for reasons to be discussed further hereinbelow. A pair of needle halves 13,14 are provided, each half 13,14 being adapted to being secured to its respective handle portion 11,12. A locking key 15 is provided adapted to secure handle portions 11,12 together as will be discussed. Stylet holder 16 is also provided comprised of a collar 17 adapted to receive therein a needle holder or stylet 18 having a needle 19 included therewith.

Figure 3:
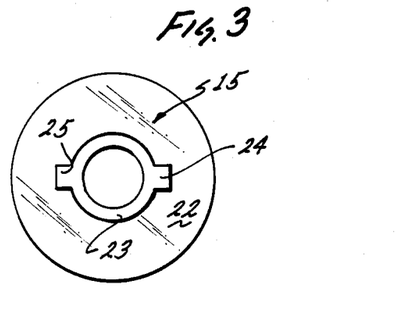
FIG. 3 is a view taken along lines 3—3 of FIG. 2.
Figure 4:
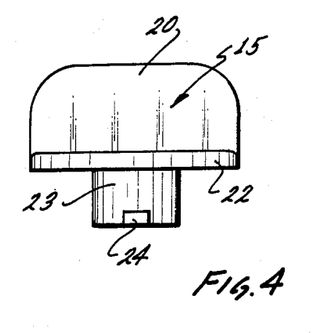
FIG. 4 is a side view of the key of FIG. 2.

Key 15 is shown in detail in FIGS. 2 to 4. Key 15 (FIG. 2) has an upstanding semi-circular flange 20 (see also FIG. 4) thereon for ease in grasping and turning the same. Flange 20 acts as a handle or grasping portion and is thus upstanding from and extending normal to a circular boss 22 (see also FIG. 3) having a hollow cylindrical member 23 extending downwardly therefrom at generally the middle thereof. Cylindrical member 23 has a pair of spaced ears 24,25 at the lower end or bottom thereof extending outwardly therefrom as shown in FIGS. 3 and 4.

Figure 5:
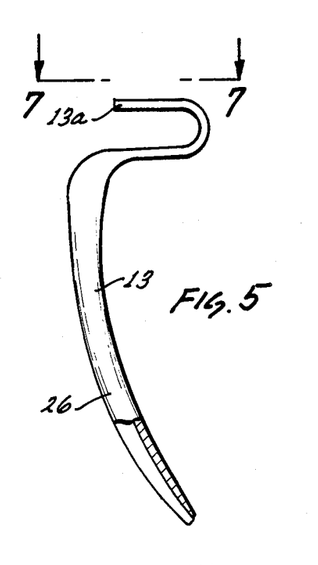
FIG. 5 is a vertical view of one of the needle halves of the device of FIG. 1.
Figure 6:
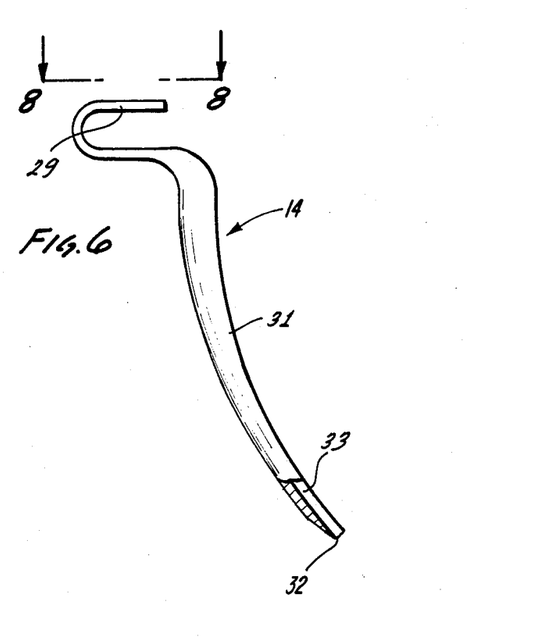
FIG. 6 is a vertical view of the other of the needle halves of the device of FIG. 1.
Figure 7:
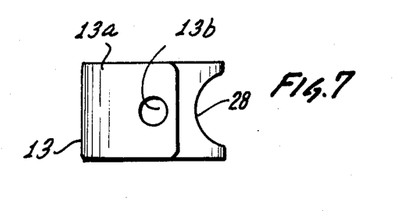
FIGS. 7 and 8 are views taken along lines 7—7 and 8—8 of FIGS. 5 and 6, respectively.

Needle halves 13,14 are shown in FIGS. 5 and 6, respectively. Needle half 13 is attachable to upper handle portion 11 and includes a U-shaped end 13a having an opening 13b (see also FIG. 7) to receive a screw (FIG. 1) therein. Needle half 13 includes a curved blade 26 extending from end 13b. Blade 26 has a radius of curvature of about 40 degrees and terminates in a sharpened flat tapered end 27 (see FIG. 1). As seen in FIG. 7, blade 26 is generally arcuate in cross-section forming a trough 28.

Figure 8:
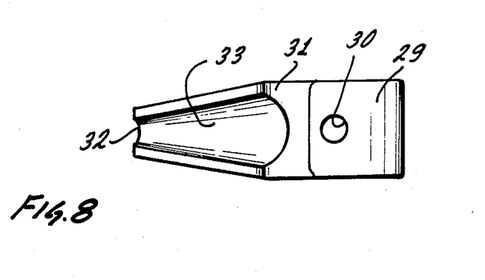

Needle half 14, shown in FIG. 6, also includes a U-shaped end 29, similar to 13a, having a like opening 30 therein (see also FIG. 8) and a blade 31 also terminating in a sharpened end 32 and also having an arcuate cross-section forming a trough 33 (FIG. 8) and also having a radius of curvature of about 40 degrees. It can be appreciated that, when brought together, as will be discussed, the troughs 33,28 mate to form a cylindrical chamber through blades 26,31.

Figures 9, 10, 11, 11A:
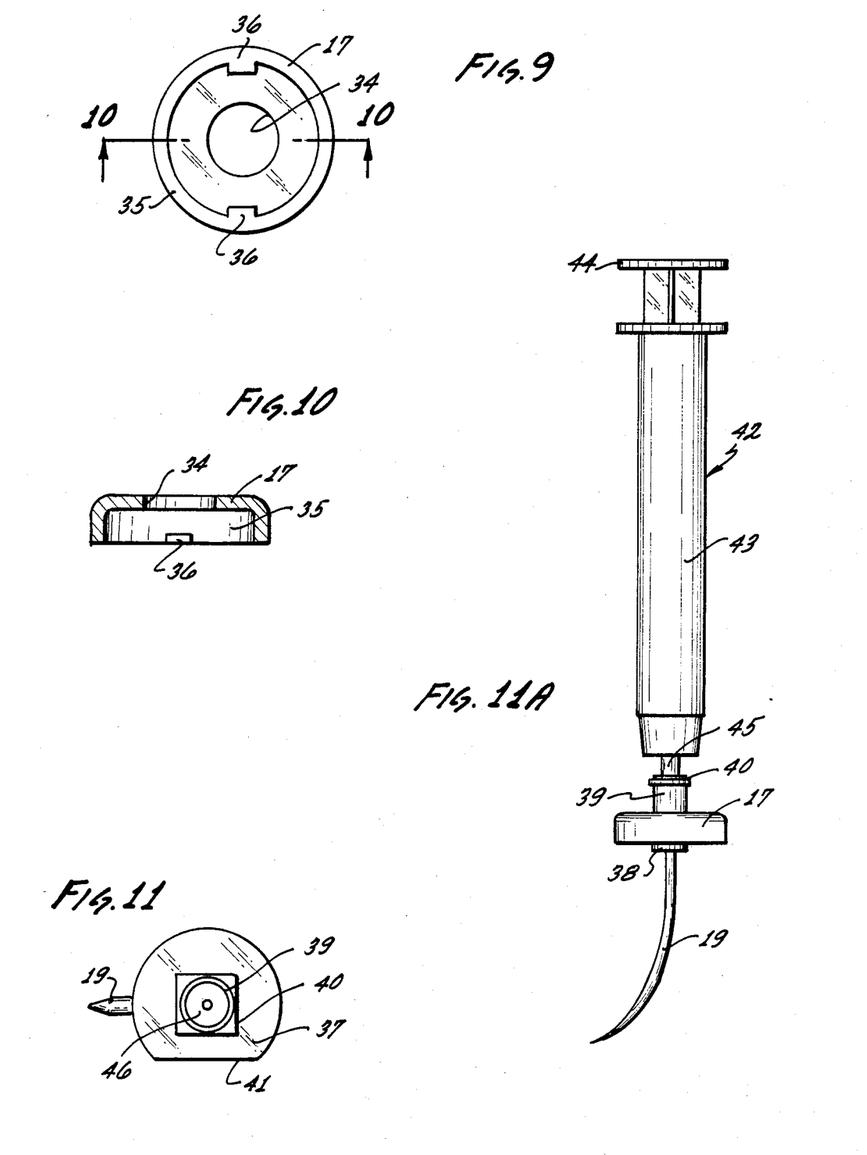
FIG. 9 is a view taken along lines 9—9 of FIG. 1.
FIG. 10 is a view taken along lines 10—10 of FIG. 9.
FIG. 11 is a view taken along lines 11—11 of FIG. 1.
FIG. 11a is a vertical view of the syringe alone of FIG. 20.

The stylet holder 16 will now be discussed. Stylet holder 16 includes collar 17 which, as shown in detail in FIG. 9, includes a throughbore 34 and a peripheral flange 35 having a pair of inwardly extending lips or ears 36 (see also FIG. 10). As seen in FIG. 1, needle holder 18 includes a flange 37 having cylindrical bosses 38,39 on opposite sides thereof. Curved needle 19 is secured in boss 38. As shown in FIG. 11, boss 39 terminates in a square-shaped collar 40 smaller in width than opening 34 in collar 17. Flange 37 is about the same diameter as the opening between peripheral flange 35 in collar 17. However, as seen in FIG. 11, flange 37 has a flattened portion 41 which enables the flange 37 to pass ears 36 when collar 40 is inserted into opening 34 and flange 37 enters the opening in collar 17 formed by flange 37. Rotating the needle holder 18 within collar 17 moves flattened portion 41 within the collar 17 thus trapping needle holder 18 therein.

The assembly of collar 17 to needle holder or stylet 18 is shown in FIG. 11a. Also, a conventional syringe 42 having a cylindrical main body 43 and plunger 44 or obturator is shown as assembled to collar 17 and stylet 18. As seen, the lower end of cylindrical main body 43 terminates in a cylindrical end 45 which is adapted to be inserted into the opening 46 in boss 39 (see also FIGS. 1 and 11). In this manner, a conventional syringe is quickly and easily assembled to the device 10.

Figure 12:
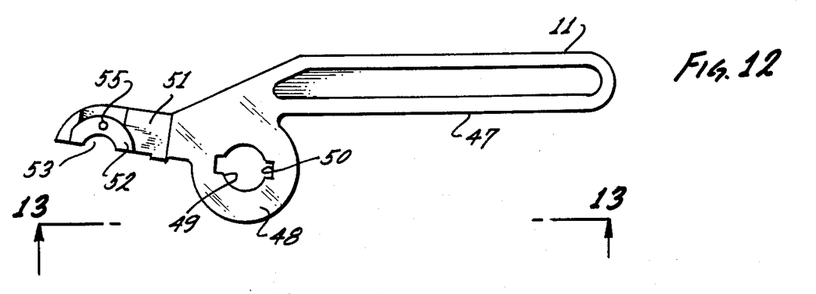
FIG. 12 is a top plan view of handle portion alone.
Figure 13:
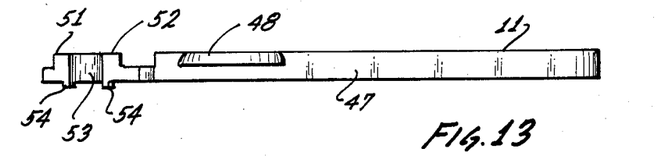
FIG. 13 is a view of the handle portion of FIG. 12 taken along lines 13—13 of FIG. 12.
Figure 14:
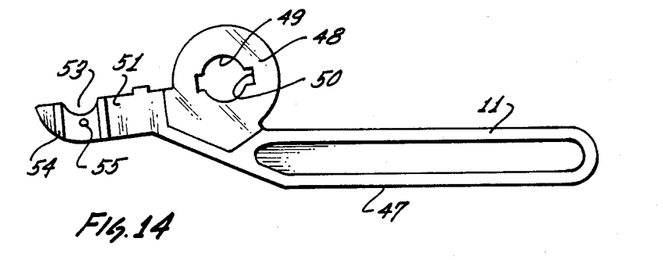
FIG. 14 is a bottom plan view of the upper handle portion alone of FIG. 1.

The handle portions 11,12 will now be described. Upper handle portion 11 is shown in FIGS. 12 to 14. Lower handle portion 12 is shown in FIGS. 15 to 17.

Looking at FIGS. 12 to 14, handle portion 11 has an enlarged handle 47 extending from a circular flange 48 having an opening 49 therethrough. Opening 49 has a pair of oppositely spaced cut-outs 50 therein. As seen in FIG. 12, handle 47 extends angularly from flange 48 and extension portion 51 extends from handle portion 47 generally parallel to a line passing through ears 50. Extension portion 51 includes an upstanding semi-circular boss 52 forming a semi-circular portion 53 in extension portion 51. As seen in FIG. 14, a pair of spaced ribs 54 are provided on the underside of extension portion 51 on both sides of portion 53 acting as guides for the needle half 13. An aperture 55 is also provided for screw 56 (FIG. 1).

Figure 15:
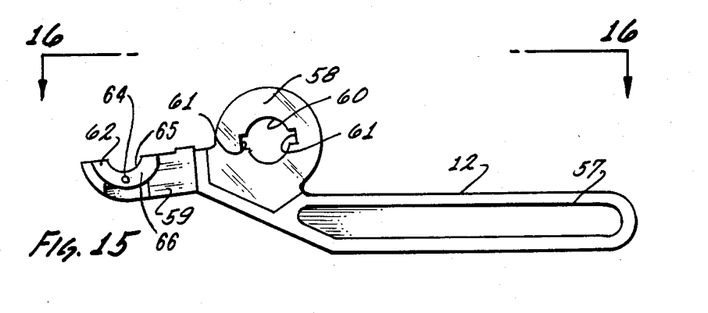
FIG. 15 is a top plan view of the lower handle portion alone of FIG. 1.
Figure 16:
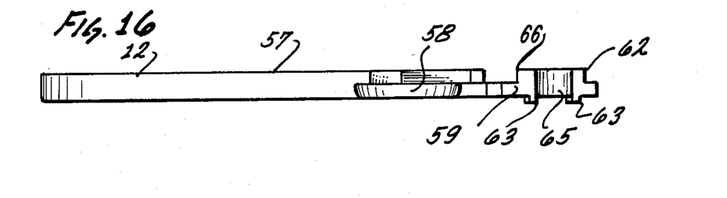
FIG. 16 is a view taken along lines 16—16 of FIG. 15.
Figure 17:
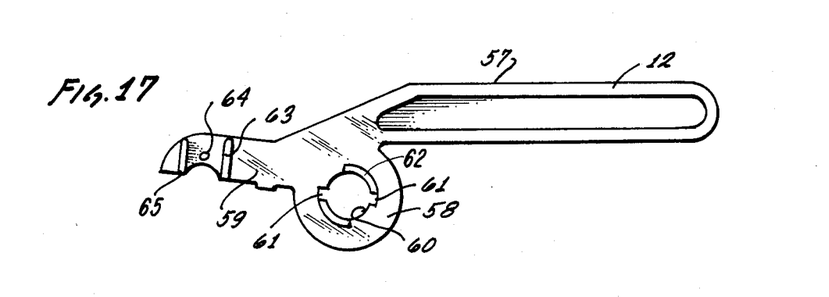
FIG. 17 is a bottom plan view of the lower handle portion alone of FIG. 1.

Handle portion 12 in FIGS. 15 to 17 is similar to handle portion 11 and also includes a handle 57, a flange 58, and extension portion 59. As seen in FIG. 15, opening 60 in flange 58 also has spaced ears 61 but also has reduced thickness semi-circular areas 62 internally of opening 60 between ears 61 FIG. 17. Ribs 63 are on the surface of extension portion 59 surrounding semi-circular area 65 and an aperture 64 for receiving screw 56 (FIG. 1) extending therethrough. As seen in FIGS. 15 and 16, a semi-circular boss 66 surrounds and/or forms portion 65.

Figure 18:
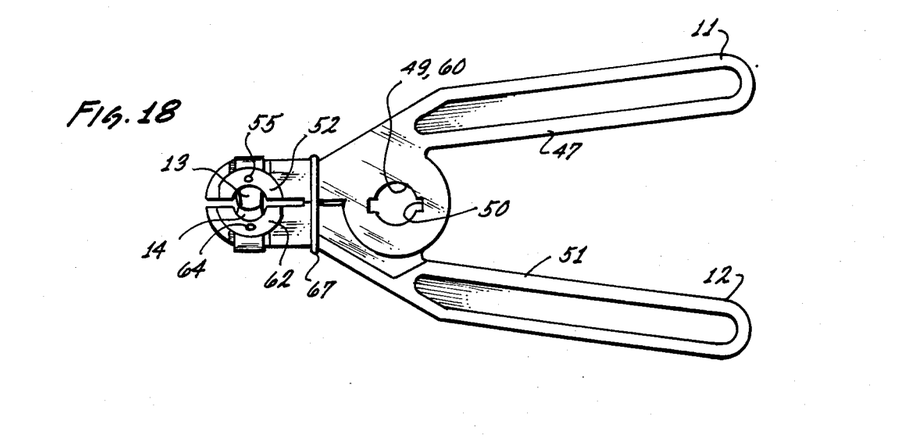
FIG. 18 is an assembled view of the upper and lower halves of the device of FIG. 1.
Figure 19:
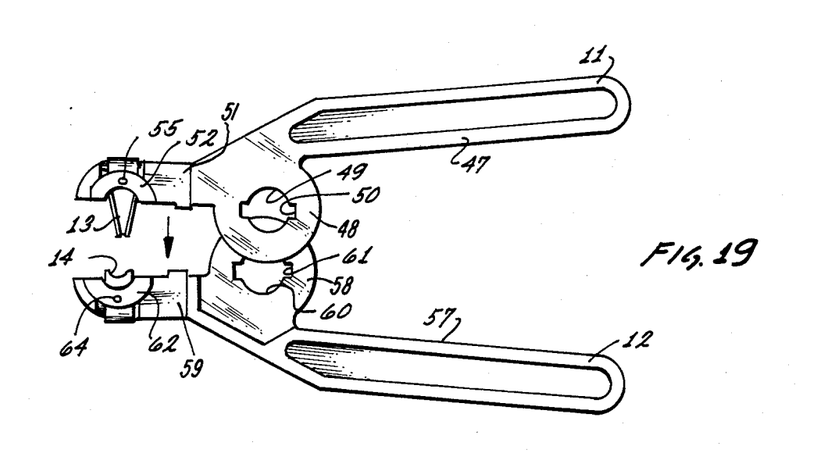
FIG. 19 is a detailed view of the assembled halves of FIG. 18 prior to insertion of the locking key therein.

The final assembled position of upper and lower halves 11 and 12 is shown in FIG. 18. The flange 48 is placed on top of flange 58 and the extension portions 51,59 are brought together as shown. As seen in FIG. 19, the openings 49,60 line up so that ears 50 and 61 are also aligned. The key 15 of FIGS. 1 to 4 is now inserted, the ears 24,25 on key 15 entering aligned ears 50,61 and portion 23 entering aligned openings 49,60. Handle portion 20 on key 15 is rotated clockwise so that ears 24,25 move into the semi-circular portions 65 of lower handle portion 12 (FIG. 15). In this manner, the handle portions 11,12 are removably locked together until it is desired to disassemble them by merely reversing the rotation of key 15 to return the ears 24,25 to alignment with ears 50,61 (when handle portions 11,12 are in the FIG. 18 position) to release the handle portions 11,12 from interengagement. If desired, a resilient member, such as a rubber band 67 (FIG. 18) may be disposed about extension portions 51,59, as shown, to bias the handle portions 11,12 together and allow the portions 11,12 to re-engage when the handles 47,57 are squeezed together to release whatever is being grasped between portions 53,65.

Figure 20:
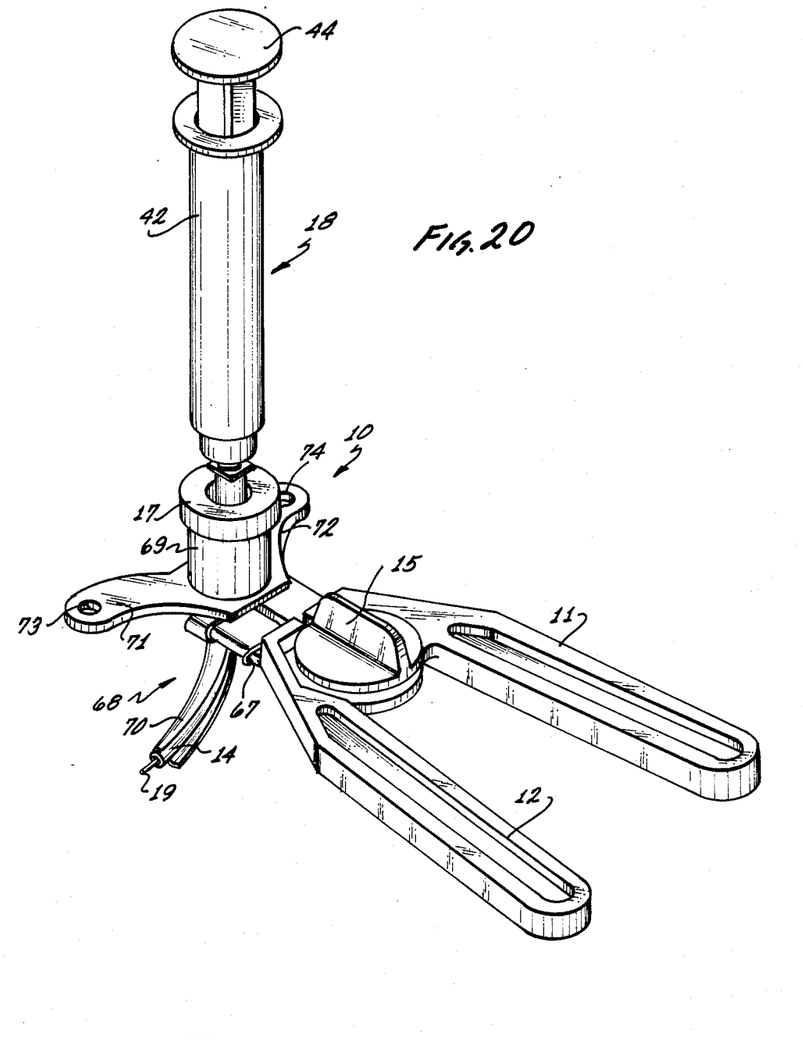
FIG. 20 is an assembled perspective view of the device of FIG. 1 showing a tube and stylet clasped therebetween.
Figure 21:
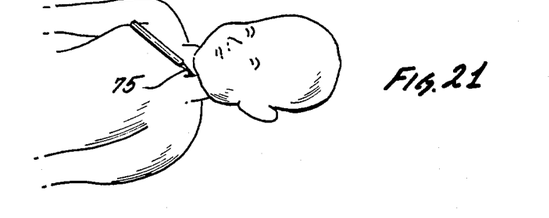
FIGS. 21 through 26 are successive illustrative views of the application of the device of FIG. 20 to perform a cricothyrotomy.

The assembly of the device of FIG. 1 is shown in FIG. 20. As seen, and as previously discussed, locking key 15 is inserted into the openings 49,60 in handle portions 11,12 and band 67 is encircled about extension portions 51,59. Syringe 42, with obturator 44, is assembled to the stylet 18 (FIGS. 1 and 12) as heretofore discussed. Needle 19 is inserted into a conventional tube 68 which is clasped between needle halves 13,14 as shown. Tube 68 has an upper cylindrical portion 69 and a lower cylindrical portion 70, portion 69 being greater in diameter than portion 70 with a throughbore therebetween. Flanges 71,72 extend from opposite sides of portion 69 at the intersection thereof with lower portion 70, and each flange is apertured, at apertures 73,74 for securing, via linear elements in apertures 73,74, tube 68 to the patient.

Figure 22:
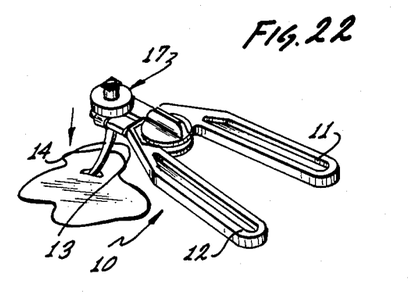
Figure 23:
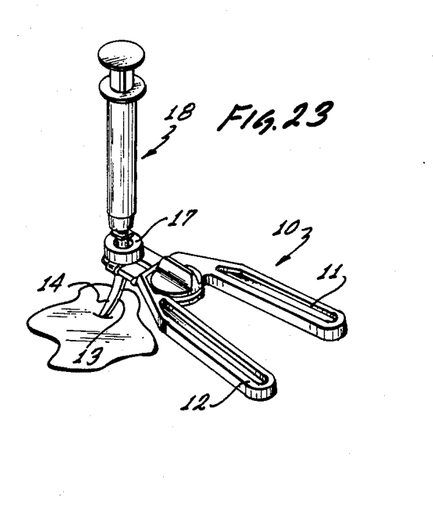

The actual application of the device 10 to perform a cricothyrotomy is illustrated in FIGS. 21 to 26. The patient is shown as a young child. A knife blade 75 is used to incise the skin to a predetermined depth, such as two centimeters. As shown in FIG. 22, needle 19 punctures the membrane just beyond entry. The syringe 42 is installed in the device 10 and the easy or free movement of the obturator 44 denotes entrance into the trachea 76. As seen in FIG. 23, the tube 68 is not held in the device 10 at this stage of the operation. The aforementioned opening in collar 17 formed by flange 35 fits onto the boss formed by mating boss halves 52,66 (i.e., halves 52,66 abut and form a circular boss which enters the opening in collar 17 formed by flange 35).

Figure 24:
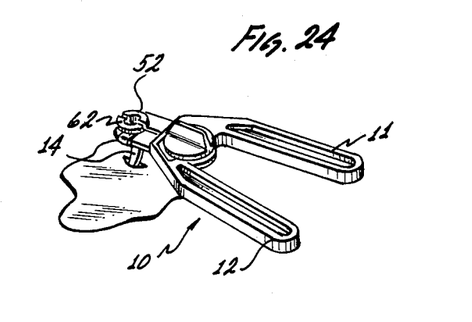
Figure 25:
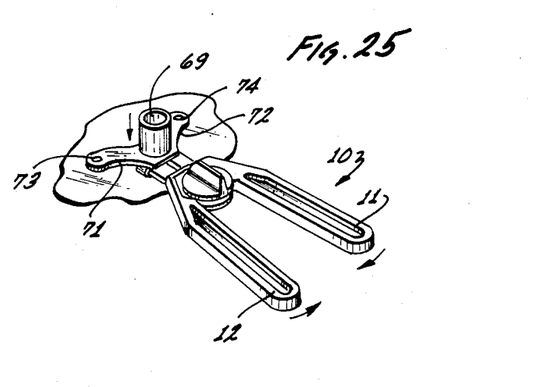
Figure 26:
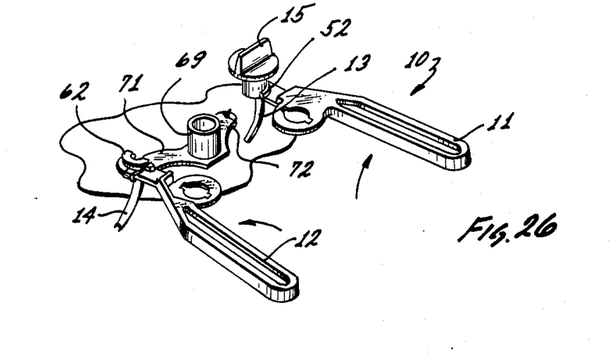

The stylet 18 and syringe 42 are now removed and the blunt needle ends 29,32 are moved further into the trachea 76. A free rocking motion of the needle portions 13,14 confirms proper depth of insertion (FIG. 24). The handles 47,57 are now squeezed and a tracheal tube, such as aforementioned tube 68, is inserted between the needle halves 13,14 as heretofore discussed. The stylet 18 is removed. The apertures 73,74 are used to secure the tube 68 to the patient. Now, as particularly contemplated in the invention, the device 10 can be removed without disturbing tube 68 which extends into the trachea 76. Thus, as shown in FIG. 26, the band 67, if used, has been removed. Key 15 has been removed by merely turning it counterclockwise to disengage the ears 24,25. Upon removal of key 15, the handle portions 11,12 separate and thus the needle halves 13,14 carried thereby also separate and are also removed along with handle portions 11,12. In suummary, the cricothyroid membrane lying in the space between the thyroid and cricoid cartilages (just below the laryngeal prominence), can be identified by a dip or notch-like effect or the first tracheal ring section of the trachea (if possible). The knife blade then incises the skin area, approximately 1 to 2 cm. The needle 19 then punctures the cricothyroid membrane in the midline. This is a vertical approach with the curved needle 19 penetrating the tissues and then turning needle 19 slightly caudadly and more horizontally to bring syringe 42 and the upper components into a more vertical position (from the acute angulation which it had at first penetration). The stylet 18 with the syringe 42 attached is used to determine depth penetration. An easy moving syringe obturator 44 on withdrawal denotes tracheal entrance. Once this has occurred, the syringe 42 and stylet components are removed together by rotating collar 17 and lifting out. The blunt edge of the needle halves 13,14 are now moved further into the trachea. Air flow through the instrument 10 at this point is obvious. A freely rocking instrument 10 also indicates no over penetration. The handle portions 11,12 of the instrument 10 are squeezed so as to spread the needle halves 13,14 in the incision site. The airway tube and obturator are inserted together through the opening created by the needle halves. It is very important at this time that the operator lift the instrument blade point slightly upwardly in order to align the needle portions 13,14 in a more horizontal position prior to inserting the airways (tube and obturator). The obturator 44 is immediately removed. At this point of the procedure, the instrument 10 may be left in place until it is medically sound to remove it. An operating or emergency room may also be selected before removal. In order to remove instrument 10 while leaving the airway in place, key 15 is removed as heretofore discussed. The tracheal tube 68 is grasped with one hand to hold it in place while removing the handle portions 11,12 in order to avoid accidental extubation as heretofore discussed. A universal adapter (not shown) may be fitted to the top of the housing of the tracheal tube 68, if desired. Expansion of the lungs may be started by mouth to airway respiration.

Overpenetration, with its disastrous consequences, is not likely to occur with the device of the invention. The mechanical force required to overcome tissue resistance is not applied at the point of the needle but at the junction of the needle and housing. The advantages of making an incision is for better visualization of the area, avoidance of subcutaneous emphysema and easy expansion of the instrumentation.

The needle 19 punctures the membrane in a vertical direction, then is rotated caudad according to its curved shape and directed into the long axis of the tracheal tube. This is done to avoid overpenetration. Easy withdrawal of the obturator 44 of the syringe 42 indicates proper depth and tracheal entrance.

Advancing the needle halves 13,14 with the stylet 18 removed offers assured positioning within the trachea and, at this point, expulsion of air through the instrument 10 may be noted. Spreading the needle halves 13,14 by squeezing on the handles 11,12 allows one to insert the tracheal tube 68 quickly and with ease into the trachea. The size of tube 68 is determined by the operator and, if unsatisfactory, may be removed and another sized tube may then be reinserted without loss of the airway. It is important that one lifts the instrument 10 up slightly before inserting the tracheal tube 68. This avoids directing the tracheal tube down against the posterior wall.

The obturators 44 of the tubes (or any other suitable obturator) prevent obstruction of the airways when they are introduced and maintain the firmness of the tube upon insertion. Tube 68 may be either taped to the patient or secured as heretofore discussed.

It can be seen that disastrous extubation complications, such as may occur if a tube is accidentally removed by the blades clasped around the tube, are avoided since each blade or neddle half can be individually removed. The locking key 15 allows for simple, quick and efficient reassembly of the instrument 10 which is essential in emergency situations. The needle blades or halves 13,14 are curved to avoid overpenetration. This is brought about when the initial penetration of the needle point occurs as the advancement is back into a horizontal plane away from the posterior wall. The needle blades or halves 13,14 and stylet 18 form a smooth, penetrating instrument which is necessary to penetrate the tough fibrous wall of the trachea in a small child.

Needle halves 13,14 are bolted or otherwise secured to handle portions 11,12 and this avoids shifting or side movement of the needle halves 13,14 which maintains an airway. If the user is compelled to manipulate the instrument 10 in a smaller area, the housing is much smaller than known instruments and the handling of the blades or halves 13,14 are off to the side of the operating arena so as to allow better visualization and easier instrumentation.

It can be seen that I have disclosed an improved surgical device for performing emergency cricothyrotomies/tracheotomies particularly useful in operating on young children.

Figures 27, 28, 29, 30, 31, 32:
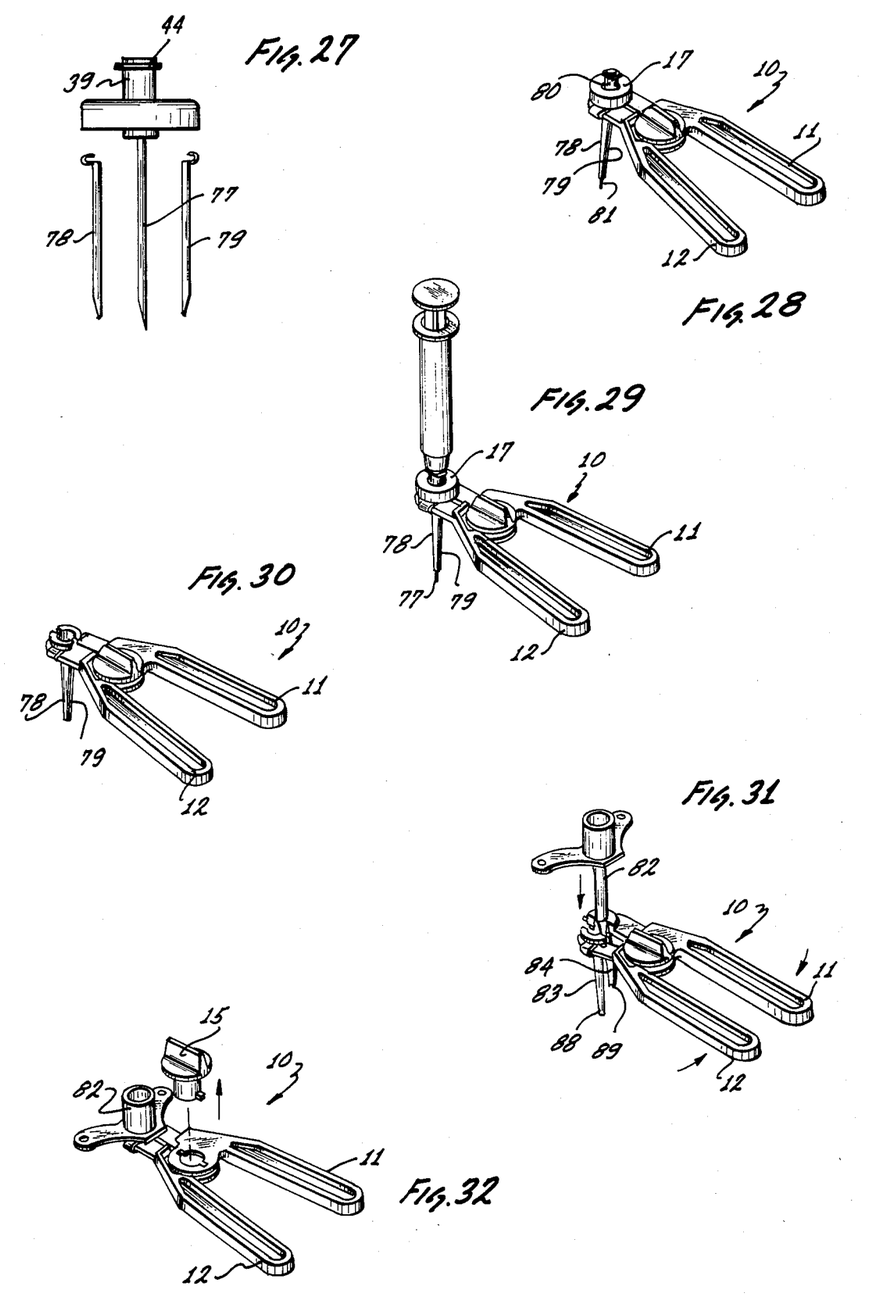
FIG. 27 is a vertical view of a modified stylet and a pair of straight needle halves prior to assembly.
FIGS. 28 through 32 are successive illustrative views of the application of the device of FIG. 1, with the modified stylet and needle halves of FIG. 27, to perform a thoracostomy.

Although curved needle halves 13,14 have been disclosed, along with a curved stylet 19 as shown in FIG. 27, a straight needle or stylet 77 may be used held with collar 17 as heretofore disclosed wherein like parts refer like parts of FIG. 12.

Thus, stylet 77 can be held by device 10 and be used to perform other operations, such as thoracostomies. In such operations, the chest skin is incised and the needle provided by needle halves 79,79 (otherwise identical to halves 13,14 and attached to handle portions 11,12 as heretofore discussed) is used to puncture into the pleural cavity (FIG. 28). Easy movement of obturator 44 denotes entrance into the pleural cavity and the locking collar 17 and stylet 77 and syringe 42 can be removed from the handles portions 11,12. The handle is squeezed apart to spread needle halves 78,79 and a chest tube 80 with a stylet 81 attached thereto being inserted between halves 78,79 (FIG. 30). The needle halves 78,79 and handle portions 11,12 are now removed with the tube 80 held during removal. The stylet 81 is now removed from tube 80 (FIG. 32).

The modified device of FIGS. 27 to 32 may also be used in like manner to perform a laparoscopy. Further, in both thoracostomies and laparoscopies, negative air pressure in the chest cavities, and gas added into the abdomen for the purpose of separating the abdomen wall from the intestines to carry out the operation, create special problems. In these cases, there is a need for closing off the escape of air or release of gas when the stylet is removed from the needle halves. For example, as heretofore discussed with respect to FIG. 29, the stylet 77 is removed from between the needle halves 78,79. This could result in the undesired escape of air from the chest cavities or release of gas from the abdomen cavity.

Thus, as shown in FIG. 33, a straight stylet 82 is provided otherwise similar to stylet 81. A pair of straight needle halves 83,84, otherwise similar to halves 78,79, are also provided. The stylet 82 is adapted to be inserted between halves 83, 84 when such halves are held together via handle portions 11,12 and related structure. Of course, stylet 82 is also provided with collar 17 and related structure. However, as seen in FIG. 33, the terminal end of stylet 82, which of course is hollow and has a terminal opening 85 at its sharpened end 86, is flared or bulged outwardly at 87 to form a peripheral outer enlarged surface. The needle halves 83,84 are also conventional terminating in sharp ends 88,89 and of course configured internally as needle halves 13,14 (FIGS. 5 and 6), but include a concave portion 90 on the inner wall of one of the needle halves, such as needle half 83, and a convex portion 91 on the other needle half, such as needle half 84. Convex portion 91 is adapted to receive therein concave portion 91 in substantially a fluid tight manner. It can be appreciated that the bulged surface 87 of stylet 82 abuts against the ends 88,89 when stylet 82 is inserted between needle halves 83,84. This engagement stops the flow of air back out of the chest cavity or gas from the abdomen cavity. However, when stylet 82 is removed from between halves 83,84, in the direction of arrow 92, the halves separate to allow removal, then move together with convex surface 91 entering concave surface 90 again sealing off air or gas flow. In this manner, an improved needle is disclosed which can be utilized with the device disclosed herein to perform improved thoracostomies or laparoscopies.

It can be seen that I have described an improved instrument for performing thoracostomies and laparoscopies wherein the holder or instrument 10 is quickly and easily removed so one can suture around the chest or abdomen tube without need for disturbing or removing the tube.

I claim:

1. In a surgical instrument comprising:
   a pair of upper and lower handle portions, each of said handle portions having an elongated handle at one end and an extension portion at the other end, each of said extension portions having a generally semi-circular opening therethrough on one side thereof, said handle portions being independent of each other and adapted to abut against each other so that said handles extend in a direction substantially parallel to each other but spaced therefrom with said extension portions abutting against each other such that said semi-circular openings abut against each other with said openings forming a generally circular opening;
   each of said handle portions having a flange intermediate said handle and said extension portion, each of said flanges having an opening therethrough, said last-mentioned openings being adapted to coincide with each other to form a single opening through said flanges when said handle portions are abutted against each other as heretofore stated;
   a key member removably mounted in said single opening, said key member and said openings in said flanges having key means therein keying said key member within said single opening so that said key member can quickly and easily lock said handle portions together or be removable therefrom to release said handle portions from engagement with each other; and
   a straight needle half secured to each extension portion extending downwardly from said semi-circular opening, each of said needle halves having an inner groove terminating at their terminal ends in sharp edges, each of said grooves being aligned with its respective semi-circular opening so that, when said handle portions abut against each other as heretofor stated, said needle halves form a generally circular channel communicating at one end with the exterior of said extension portions and at the other end with said sharp edges, a semi-circular boss on each of said extension portions above said semi-circular openings therethrough and coinciding therewith, said semi-circular bosses being adapted to form a circular boss when said handle portions are in an abutting position as heretofore stated, a stylet having a straight needle at one end and a hollow tubular member at the other end holding said needle, said tubular member having an upper flange at one end and a lower flange at the other end, and a collar having an upper opening therein for receiving said upper stylet flange therethrough and a lower opening, said lower stylet flange being receivable within the lower opening of said collar and retained within said collar with said upper stylet flange extending out of the upper opening in said collar and the lower stylet flange extending out of the lower opening in said collar, said lower opening of said collar receiving said circular boss therein with said needle extending downwardly between said needle halves and said tubular member between said upper and lower flanges disposed between, and retained within, said semi-circular openings, said needle extending below the terminal ends of said needle halves when said stylet is retained between said extension portions, said needle terminating in a sharp end having a bulged portion abutting against the terminal ends of said needle halves so that fluid cannot flow between said sharp end and said terminal ends, said needle halves having cooperating means thereon adjacent said terminal ends preventing fluid flow through said needle halves when said needle is removed from between said needle halves, said cooperating means including one of said needle halves having a concave portion therein between said extension portion and said terminal end adjacent said terminal end and the other of said needle halves having a convex portion therein between said extension portion and said terminal end adjacent said terminal end, said convex portion mating with said concave portion to seal off fluid flow.

* * * * *